United States Patent
Hertz

(10) Patent No.: US 6,951,505 B2
(45) Date of Patent: Oct. 4, 2005

(54) METHOD USING HANDHELD APPARATUS FOR DELIVERY OF PARTICULATE MATTER

(76) Inventor: Reuben Hertz, 2318 Sea Island Dr., Fort Lauderdale, FL (US) 33301

(*) Notice: Subject to any disclaimer, the term of this patent is extended or adjusted under 35 U.S.C. 154(b) by 0 days.

(21) Appl. No.: 10/704,517

(22) Filed: Nov. 8, 2003

(65) Prior Publication Data

US 2004/0137825 A1 Jul. 15, 2004

Related U.S. Application Data

(60) Continuation of application No. 09/939,865, filed on Aug. 27, 2001, which is a division of application No. 09/196,498, filed on Nov. 21, 1998, now Pat. No. 6,287,180, which is a division of application No. 08/517,379, filed on Aug. 21, 1995, now Pat. No. 5,839,946.

(51) Int. Cl.[7] ................................................. B24C 7/00
(52) U.S. Cl. ........................................ 451/38; 451/90
(58) Field of Search ............................ 451/102, 90, 38, 451/99

(56) References Cited

U.S. PATENT DOCUMENTS

| | | | |
|---|---|---|---|
| 2,133,149 A | 10/1938 | Poncelet | |
| 2,441,441 A | 5/1948 | Paasche | |
| 2,577,465 A | 12/1951 | Jones et al. | |
| 2,612,732 A | 10/1952 | Ziegler | |
| 2,641,087 A | 6/1953 | Greiser | |
| 2,696,669 A | 12/1954 | Ikse | |
| 2,725,684 A | 12/1955 | Crowe | |
| 2,744,361 A | 5/1956 | Larson et al. | |
| 3,164,153 A | 1/1965 | Zorzi | |
| 3,626,841 A | 12/1971 | Schachter | |
| 3,631,631 A | 1/1972 | Greenstein | |
| 3,981,479 A | 9/1976 | Foster et al. | |
| 4,032,474 A | 6/1977 | Goudriaan et al. | |
| 4,174,571 A | 11/1979 | Gallant | |
| 4,287,812 A | 9/1981 | Iizumi | |
| 4,369,607 A | 1/1983 | Bruggeman et al. | |
| 4,391,590 A | 7/1983 | Dougherty | |
| 4,475,370 A | 10/1984 | Starke et al. | |
| 4,646,782 A | 3/1987 | Ezekoye | |
| 4,673,051 A | 6/1987 | Dairling et al. | |
| 4,941,298 A | 7/1990 | Fernwood et al. | |
| 4,967,791 A | 11/1990 | Sternberger | |
| 5,123,206 A | 6/1992 | Woodson | |
| 5,289,919 A | 3/1994 | Fischer | |
| 5,330,354 A | 7/1994 | Gallant | |
| 5,368,844 A | 11/1994 | Gaffar et al. | |
| 5,839,946 A | 11/1998 | Hertz | |
| 6,004,191 A | 12/1999 | Schur et al. | |
| 6,354,924 B1 | 3/2002 | Trafton et al. | |

*Primary Examiner*—Robert A. Rose
(74) *Attorney, Agent, or Firm*—Allen D. Hertz

(57) ABSTRACT

A disposable apparatus for propelling particulate matter against a surface of a target material that includes: a mixing chamber having a chamber wall, a multi-conduit receiving port, a propellant-gas receiving conduit, and a discharge conduit. The gas delivery conduit extends from the propellant-gas receiving port into the chamber, a mixture discharge conduit extending from the mixture discharge port into the chamber, and a quantity of particulate matter inside the chamber. The disposable apparatus further includes a membrane capable of allowing a gas stream to pass through when the gas stream is flowing and seals the mixing chamber when the gas stream is not flowing. The membrane can be of a hemispherical shaped, molded piece that includes at least one slit to provide an opening when the gas stream is flowing. A method is provided for propelling particulate matter against a surface of a target material using the above-described apparatus, including the steps of delivering a stream of gas into the air delivery conduit and into the mixing chamber from the gas source, so that the gas stream blows through the quantity of particulate matter, causing the particulate matter to mix with the gas stream, forming a gas and particle mixture, and discharging the mixture through the discharge conduit and the discharge port to strike the surface of the target material. The method further provides a means for automatically containing the particulate matter within the mixing chamber when the apparatus is not in use.

23 Claims, 7 Drawing Sheets

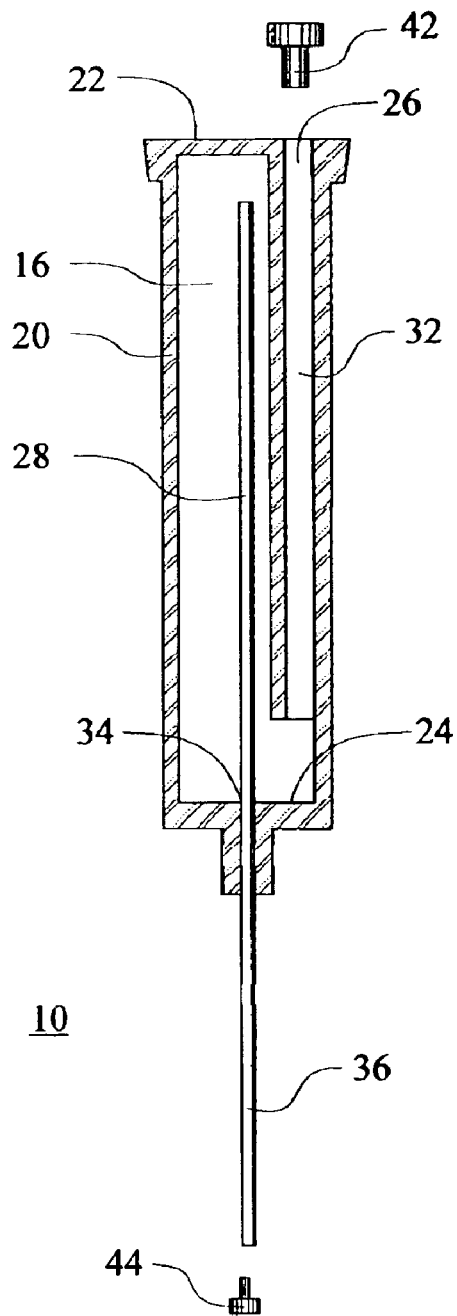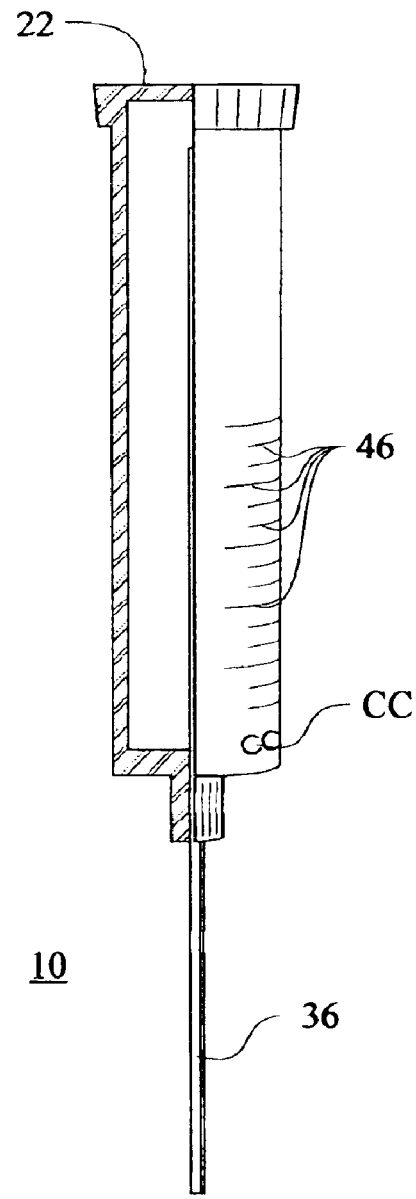
FIG. 1  FIG. 2

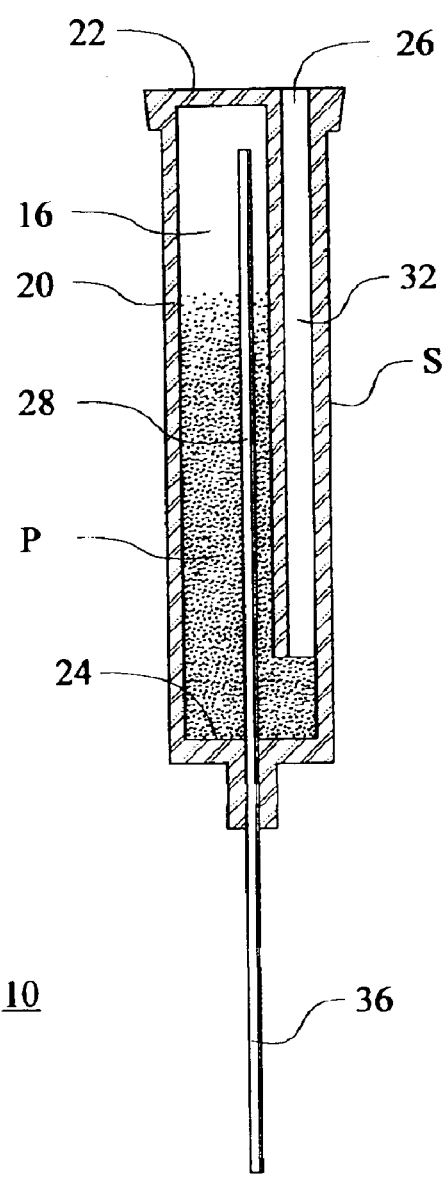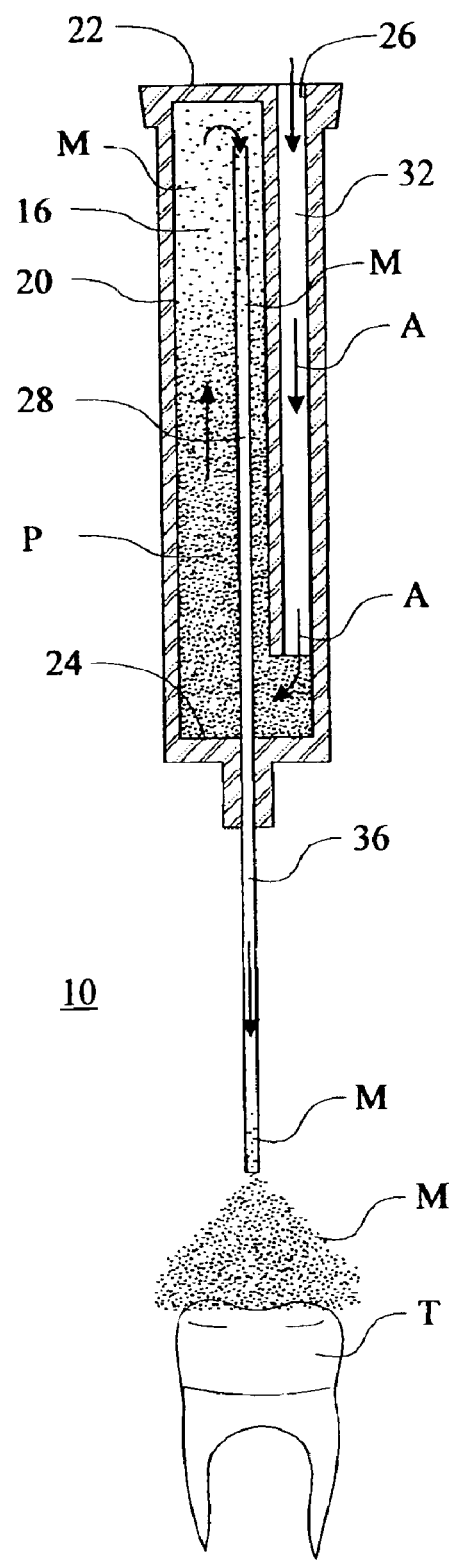
FIG. 3
FIG. 4

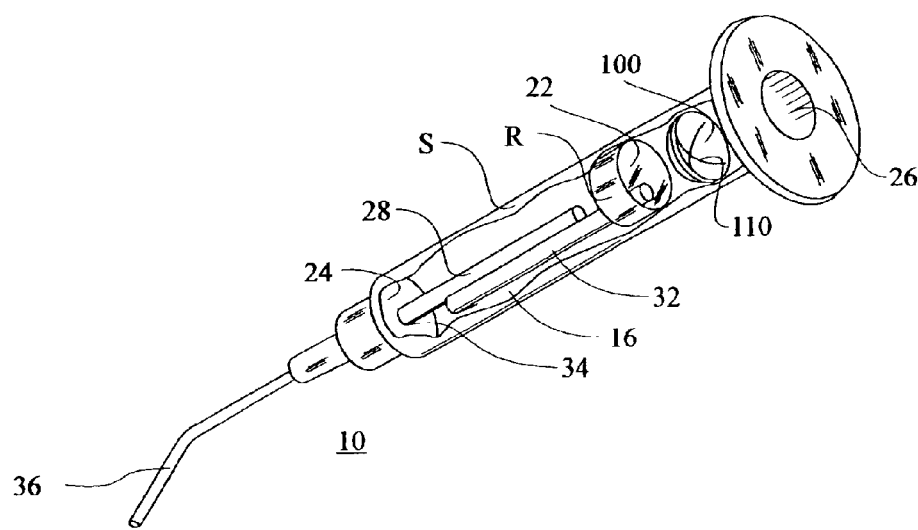
FIG. 9
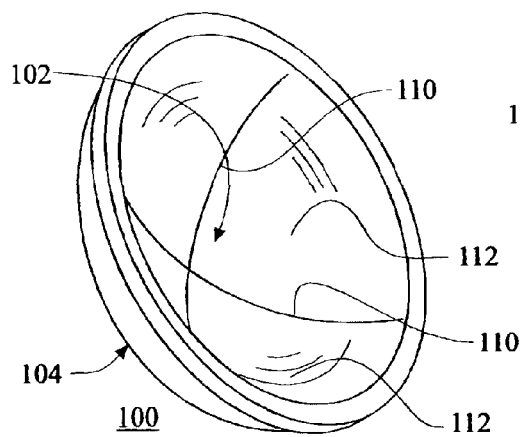 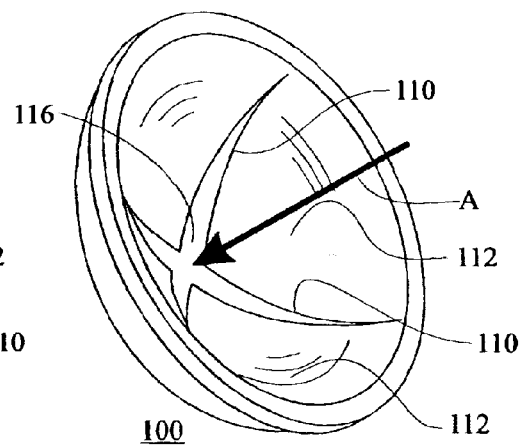
FIG. 10          FIG. 10A

METHOD USING HANDHELD APPARATUS FOR DELIVERY OF PARTICULATE MATTER

RELATED US APPLICATION DATA

Divisional Application and claiming priority to application Ser. No. 08/517,379 filed Aug. 21, 1995 now U.S. Pat. No. 5,839,946; Ser. No. 09/196,498, filed Nov. 21, 1998 now U.S. Pat. No. 6,287,180; and is a continuation of Ser. No. 09/939,865 filed Aug. 27, 2001 which are incorporated by reference herein.

FIELD OF THE INVENTION

This invention relates to a device and to a method. More specifically, this invention is directed to a self-contained device for directing a fluid stream containing particulate matter against a surface to abrade, etch, erase, cut, penetrate, smooth, clean, polish and harden the surface. In one of the preferred embodiments of the invention the particulate matter is contained within the device, and a carrier fluid, under pressure, introduced therein to produce a fluid stream that can be delivered to a target surface. The device can be powered and/or energized by a source of compressed gas that is coupled to the device through a fixture designed for that purpose. The invention also includes a method for delivery of a particle stream, under pressure, to a target surface; and, to the selective modification of the target surface depending upon the hardness of the particle, the velocity of impact and the extent of the exposure of the target surface to the particle stream.

DESCRIPTION OF THE PRIOR ART

The use of abrasives to modify the surface of an object (e.g., clean, polish, etch, etc.) is common practice in a variety of environments and professions. Typically such abrasive can take the form of a paste or free-flowing powder, and delivered to the surface of an object either manually, or through the use of a mechanical implement, or suspended in fluid (gas or liquid).

In the dental profession abrasives can be used to clean teeth and in the preparation of the dentition for bonding with various enamels and/or hardening agents. Typically the abrasive is delivered to the surface of the teeth by means of a carrier fluid stream (e.g., air or inert gas) containing a particulate abrasive. The object of such treatment is to remove foreign material, roughen or etch the surface to enhance bonding quality, or to dull an unsightly shine. As the gas and particulate matter impact the target material under pressure, the abrasive nature of the particles progressively causes layers of the target material to sheer one at a time. This process of controlled removal of material from the surface of the teeth is known as "etching".

Typically devices used in the delivery of the carrier fluid stream (e.g., air or inert gas) containing a particulate abrasive have resembled a sand blaster. More specifically, the generation of an abrasive fluid steam is accomplished by the placement of an abrasive in a reservoir and the drawing of the abrasive from the reservoir, under negative pressure, into an accelerated air or gas stream. The source of the accelerated air or gas stream is typically a pressurized gas supplied from a compressor or tank.

In operation of the foregoing devices, the particle stream is directed through a channel of a nozzle (or delivery port) having a precise channel dimension and geometry. Typically this nozzle is constructed of metal or comparable durable material. As is appreciated, the precise delivery of the particle stream requires that the channel dimensions and geometry be maintained. Unfortunately, as the abrasive stream passes through the channel of the nozzle of the device, the inside diameter of the channel is worn (and the original tolerances altered), thereby causing a loss of precision, which ultimately requires the nozzle's replacement or replacement of the entire device. Additional maintenance is also required where, during the course of use, the device is exposed to debris or bacteria and thus must be cleaned prior to re-use. Because of the foregoing demands and constraints, such devices are typically expensive and thus are generally not readily discarded, even when in need of relatively extensive repair or refurbishing. Since such devices are not generally disposable, individuals must be shied to maintain, clean refill and reassemble them. This presents an opportunity for unit malfunction from contamination of the abrasive material, and by the reloading of the device with inappropriate and even dangerous particulate material.

Examples of these prior devices include that described in Fernwood, U.S. Pat. No. 4,941,298, issued on Jul. 17, 1990. Fernwood discloses a rear-reservoir micro sandblaster that includes a hollow tubular handle with a nozzle at one end for dispensing a mixture of a solid material and a gaseous medium, and a compressed air and solid particulate material-receiving member at the other end of the handle. The nozzle section of the apparatus contains a mixing chamber where a vacuum is created by the flowing pressurized gaseous medium, drawing solid material into the chamber from a rear reservoir. Problems with Fernwood are that it is too costly to be disposable; it draws particulate matter from a container using a vacuum rather than by more efficient blow-through (turbulent or vortex) mixing of this gas as per the subject invention, and is thus very sensitive to variations in material and gas moisture levels, and requires an unclogging mechanisms, Fernwood also operates at relatively high pressures, 80–100 PSI, requiring a special tap into the air fines and limiting the range of operational pressures. In addition, The Fernwood device suffers from one or more of the following perceived deficiencies:

requires special training to set up and use,
cannot deliver varying sizes of particles,
is contaminated after every use, and
is not cost-effective and cannot be completely sterilized between use.

The apparatus disclosed in the Microetcher™ brochure (available from [insert company and address]) is similar to the Fernwood device in that it suffers from most, if not all, of the same perceived deficiencies. Other products available from various manufacturers, are similarly limited, and/or otherwise attempt to differentiate themselves from their competition by offering "improvements" relative to case of cleaning and/or sterilization, e.g., Handiblaster™ available from Mirage/Chameleon Dental Products, Inc., of [insert address); and Microetcher II™, available from [insert supplier, address].

OBJECTS OF INVENTION

It is the object of this invention to remedy the above as well as related deficiencies in the prior art.

More specifically, it is the principle object of this invention to provide a device for delivery of a fluid particle stream that includes a combined particle reservoir and particle mixing chamber integral with such device.

It is another object of this invention to provide a device for precise delivery of a fluid particle stream that is both effective and yet inexpensive and thus readily disposable.

It is still another object of this invention to provide a device for precise delivery of a fluid particle stream that is pre-charged with particulate abrasive matter.

It is still yet another object of this invention to provide a device for precise delivery of a fluid particle strewn which includes an adjustable dispensing conduit, or nozzle, for directing the flow of the fluid particle stream onto a delimited area of a target surface.

It is an additional object of this invention to provide a device for precise delivery of a fluid particle stream which includes means for introduction of the stream of fluid, under pressure, into a mass of abrasive particles within the device so as to create a turbulent mixture thereof that can be discharged via a dispensing conduit or nozzle onto a delimited area of a target.

It is a yet additional object of his invention to provide a method for precise delivery of a fluid particle stream to effect selective abrasion of a delimited area of a target.

SUMMARY OF THE INVENTION

The above and related objects are achieved by providing a device for the precision delivery of a particle stream of abrasive material to a delimited area of a target. In one of the preferred embodiments of the invention, the device comprises an essentially closed chamber having a fitting that is adapted for releasable connection to a source of pressurized fluid means for directing the pressurized fluid into a mass of abrasive particles within the closed chamber so as to generate a mixture of fluid and abrasive particles within the closed chamber and a nozzle for delivery of the fluid and particle mixture to a delimited area of a target. The term "fluid" as used herein is intended as inclusive of gases, liquids and any combination thereof. In the preferred embodiments of this invention, the source of gas is an air compressor, or pressurized canister containing & or an inert gas. The abrasive particles, which are suitable for use in this device, include aluminum oxide, sodium bicarbonate and other common polishing or grinding agents. The particle size of the abrasive should obviously be smaller than the any of the passages of the device through which they are to pass. The particle density is to a degree limited by the amount of pressure required to effect mixing thereof with the fluid in the chamber of the device and thereafter the transport/flow of the resultant mixture through the nozzle of the device.

The pressurized fluid is introduced into the chamber at or near the top of the device, and thereafter is directed through a fluid transport conduit to the base of the device where it is forced through a free-flowing mass of particulate (abrasive) matter that has been predisposed within the device at the time of its manufacture. Upon injection of the fluid into the chamber, turbulent mixing of fluid and abrasive particles occurs which mixture is and remains under substantial pressure (generally in excess of one (1) atmosphere). This is accomplished by control of the cross-sectional area of the fluid transport conduit relative to the cross-sectional area of the nozzle. The selection of a specific diameter for these two device components is a function of intended use, the particle size of the abrasive material to be delivery with such device and the desired force to be exerted upon the target by the fluid particle stream as it is expelled from the end of the nozzle onto the target surface. In the preferred embodiments of the invention, the cross-sectional dimension of the fluid transport conduit is greater than the cross-sectional dimension of the nozzle. More specifically, the inside diameter of the conduit designed for dental applications is preferably at least about 50% greater than the cross-sectional area of the nozzle and can range from about 0.01" to about 0.20", with the most preferred diameter being about 0.045". The inside diameter of the nozzle can range from about 0.005" to about 0.100", with the preferred diameter being about 0.021".

In the preferred embodiment of the invention the nozzle comprises an elongated tube fixedly positioned in an orifice in the base of the chamber, and which extends both into and from the base of the chamber. The degree of extension of the distal end of the nozzle into the chamber is calculated to contribute and promote the formation of a turbulent mixture of fluid and particles in the chamber; and, the proximal end of the nozzle, the precise delivery of the fluid stream containing the abrasive particles.

In one of the preferred embodiments of this invention the distal end of the nozzle is positioned near the top (lid) of the chamber, and above the open end of the fluid transport conduit. In addition, the relative height, or extension, of the nozzle into the chamber is also a function of the volume of abrasive particles that is to be pre-loaded into the chamber at the time of manufacture. More specifically, it is preferable that the height of the nozzle extend at least above the level of the anticipated abrasive charge, and yet be sufficiently distant from the top (lid) of the chamber to allow for turbulent mixing and channeling of the mixture into the opening at the distal end of the nozzle.

The chamber design of the device is further unique in that it provides an effective and inexpensive configuration for the precise delivery of a fluid particle stream in a disposable package.

This invention also provides a method for propelling particulate matter against a surface of a target material using the above-described apparatus, including the steps of delivering a stream of fluid (e.g. gas) into the fluid delivery conduit and from such conduit into the chamber of this device, so that the flow of the gas stream continuously blows through the quantity of particulate matter, causing the particulate matter to mix with the gas stream, forming a gas and particle mixture, and discharging the mixture through the discharge conduit and the discharge part to strike the surface of the target material.

BRIEF DESCRIPTION OF THE DRAWINGS

The drawings, which are provided and described herein, are intended to be illustrative of a number of the preferred embodiments of this invention. Where an element of an illustrated device is common to more than-one drawing, it is assigned the same reference numeral for continuity of expression and case of understanding.

FIG. 1 is a cross-sectional side view of the preferred embodiment of the inventive particle-propelling apparatus. The particulate matter and gas source are omitted.

FIG. 2 is a partial cross-sectional side view of the apparatus of FIG. 1, revealing some of the outer chamber side wall loving optional grid measuring markings and a circumferential color-code band.

FIG. 3 is a view as in FIG. 1, showing the apparatus with the particulate matter added.

FIG. 4 is a view as in FIG. 3, with the apparatus in operation discharging the gas and particulate matter mixture toward a surface of a target material.

FIG. 9 is a perspective view of an apparatus including a molded, uni-directional flow control apparatus.

FIG. 10 is a detailed perspective view of the molded, uni-directional flow control apparatus. FIG. 10A is a detailed perspective view of the molded, uni-directional flow control apparatus shown with flow applied.

DETAILED DESCRIPTION OF THE INVENTION INCLUDING PREFERRED EMBODIMENTS

Figure 2A:
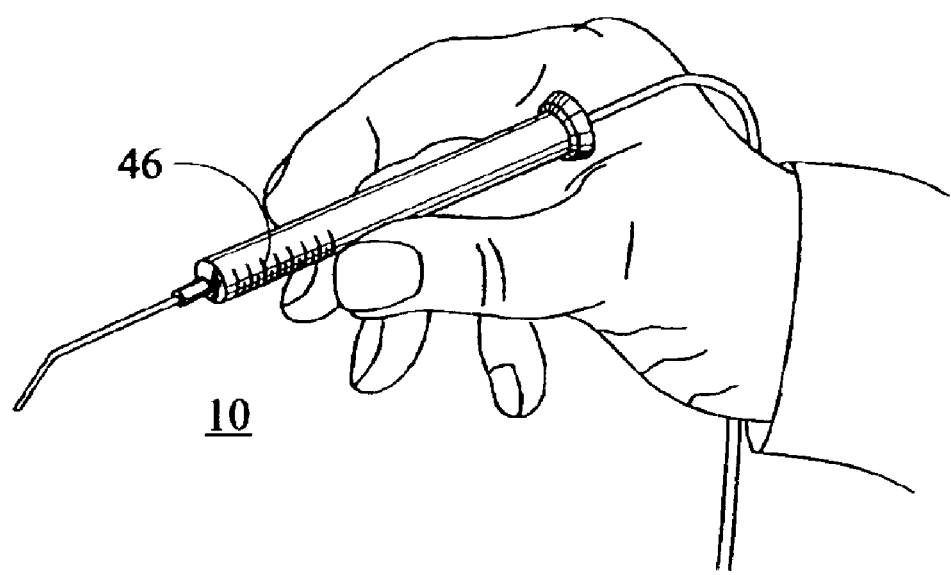
FIG. 2*a* is a perspective view of the apparatus of FIG. 2 in the hands of a user ready for operation.
Figure 5:
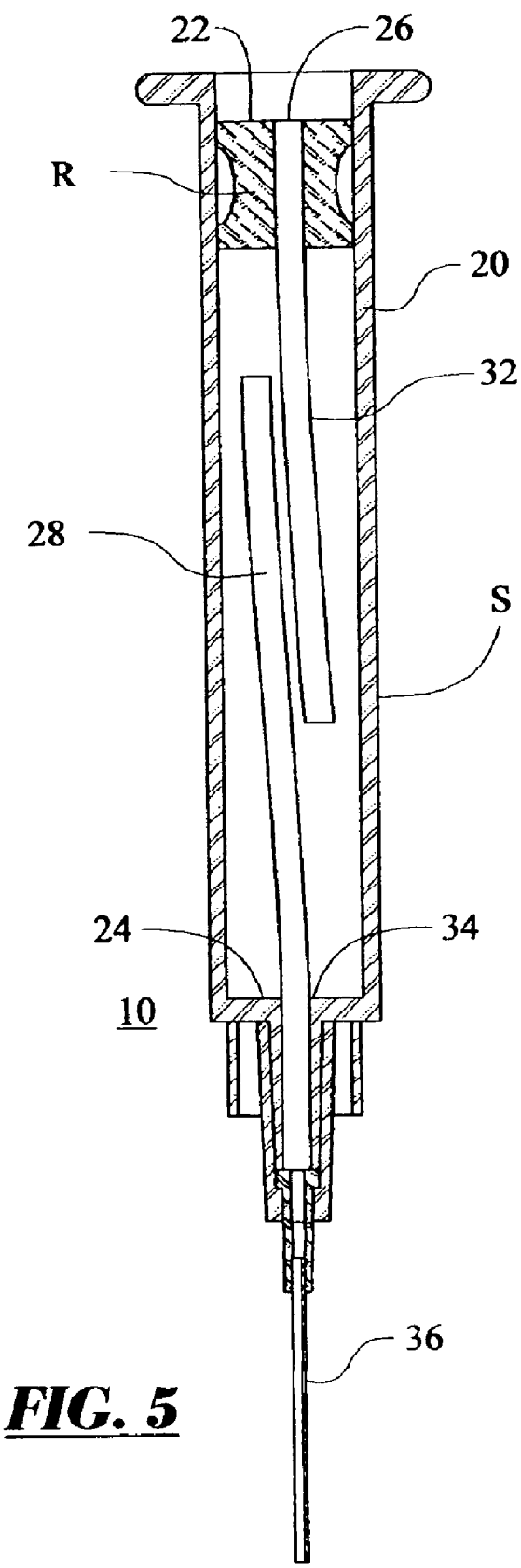
FIGS. 5 and 6 show alternative embodiments of the claimed apparatus, formed from a conventional industrial syringe.
Figure 5A:
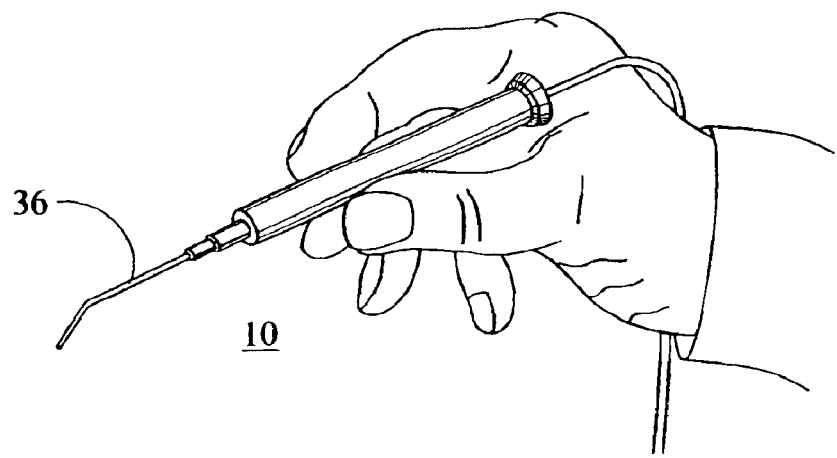
FIG. 5*a* is a perspective view of the apparatus of FIG. 5 in the hand of a user ready for operation.
Figure 6:
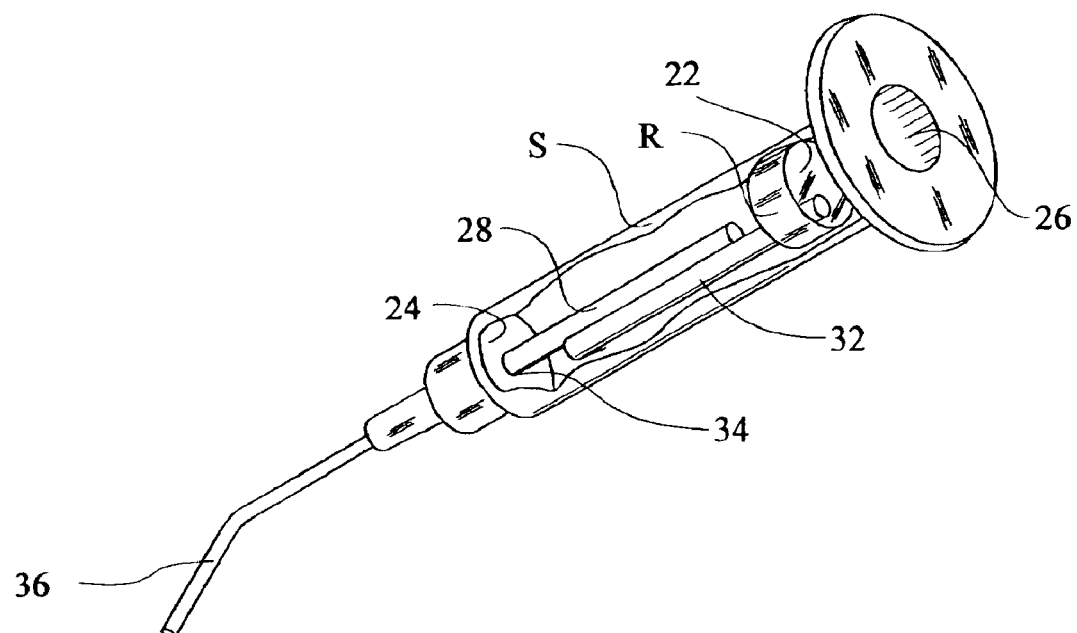

The detailed embodiments of the invention disclosed herein are representative of a number of the preferred configurations of the device.

First Preferred Embodiment

Referring to FIGS. 1–4, a disposable particle-propelling apparatus 10 is disclosed for propelling particulate matter P against target material T. The apparatus 10 includes a cylindrical mixing chamber 16 having a chamber wall 20 and two end wall portions 22 (fid) and 24 (base), respectively. Apparatus 10 is powered by a compressed gas source, such as an air compressor or a compressed gas cylinder (not shown), which connects to and is in fluid communication with the gas receiving port 26 of end wall portion 22. The gas-delivery conduit 32 extends from the gas receiving port 26 into the mixing chamber 16. End wall 24 (base) has a mixture discharge port 34. A mixture discharge conduit 28 extends in fluid communication from mixture discharge port 34 into mixing chamber 16. A particle directing tube 36 is provided in fluid communication with discharge port 34 and extends opposite discharge conduit 28 outside from mixing chamber 16. A quantity of particulate matter P is scaled inside chamber 16, the quantity being sufficient to only partially fill chamber 16, leaving space for gas and particulate water P to mix. The complete sealing of the particulate matter P gives matter P a virtually unlimited shelf life and protection from contamination (e.g. humidity). Mixing chamber 16 provides a gas-tight seal to maintain particle sterility and to prevent gas leakage during operation. An inlet cap 42 and a lip cap 44 seal gas-receiving port 26 and mixture discharge part 34, respectively, and are removed when apparatus 10 is to be connected to the compressed gas source for use. Volume grid markings 46 are preferably provided on the wall side portion 20 of chamber 16 so that the quantity of particulate matter P used can be measured and visually observed when wall 20 is constructed of a transparent or translucent material. Chamber wall 20 may also be color-coded to identify the type of particulate matter P. The color code marking CC may indicate the particle size and the type of particulate matter P. Tube 36 serves to both direct and accelerate the discharging gas and particular matter P mixture without the mixing chamber. As a result, the particulate matter P can be applied to a focused or delimited area of a target and at a uniform velocity. Since apparatus 10 is disposable, tube 36 can be fabricated inexpensively to sustain a limited use. Tube 36 is manually bendable (without crimping) thus permitting it to be quickly set to an angle without crimping, making the discharge omni-directional, and, thus, provide access to-hard-to-reach surfaces. Tube 36 preferably has a preset orifice diameter to accommodate a given size and type of particulate matter P, and is preferably made of metal, but may also be formed of suitable durable plastic or comparable material.

Chamber 16 is preferably an integrated chamber with balanced distribution of weight that is preferably slender enough to hold and manipulate as though it were a writing instrument. The direct, blow-through, turbulent mixing within chamber 16 makes apparatus 10 operational at all orientations relative to the target surface and to the direction of gravity. The slender construction makes chamber 16 able to access narrow spaces and operate in small confined areas. Chamber 16 can receive and function with varying gas pressures applied to gas-receiving port 26, selected to accelerate particles to various desired velocities for various given tasks. Turbulent mixing of particulate matters P directly in the path of the gas stream within chamber 16 enables apparatus 10 to deliver particulate matters P of a wide range of sizes, and to mix and deliver a wide range of particulate matter types. The direct, blow-through mixing in chamber 16, permits operation at very low pressures, thereby increasing the range of operational pressures that may be selected.

Apparatus 10 contains no moving parts and is preferably made of disposable plastic, so that particulate matter P and apparatus 10 can be sterilized at the factory, and apparatus 10 replaced rather than refilled and reused. Apparatus 10 is designed to with stand common sterilization techniques such as autoclave, chemical treatments and irradiation. Contemplated apparatus 10 construction materials may include but are not limited to plastic, stainless steel, Delrin™, and Teflon™. Apparatus 10 is lightweight, manufactured to be recyclable, and easy to use and replace without training or maintenance.

Apparatus 10 can be constructed from an adapted disposable syringe S of a type that is extremely common in the health care industry, see FIGS. 5 and 6. Needle 36 is attached to a standard syringe needle with a dulled tip, and formed of either metal or plastic. Gas-receiving port 26 is a hole bored into a standard rubber syringe stopper R separated from a standard syringe plunger. Mixture discharge port 34 is the existing discharge opening of the syringe S, while standard tubing can be used for gas delivery conduits 32 and 28.

Second Preferred Embodiment

FIG. 7 depicts an alternative embodiment of the invention wherein the design choice of the various component parts thereof is based, in part, upon fabrication demands dictated by injection molding constraints and manufacturing economies. More specifically, the fluid delivery conduit (32) is fabricated as an integral component of the chamber wall (20). The fluid-deliver conduit (32) is further distinct from the First Preferred Embodiment described above in that such conduit now extends the full length of the chamber to the base (24) thereof. The base (24) is also unique in that a chute (50) (as more fully illustrated in FIG. 8 described hereinafter) has been formed therein to provide for deflection of the fluid into the chamber so as to cause effective mixing of the fluid and the particle charge into a chute formed within the base of the chamber. This chute includes three distinctive functional features, namely an essentially round or bowl-like cavity (52) that roughly corresponds in overall dimension with the distal end of the fluid-delivery conduit (32). The second functional features comprises an intermediate section (54), or ascending ramp which is characterized by its progressive slope, that extends for the round or bowl-like cavity (52) to a riser (56) which directs the fluid into the chamber and thereby turbulence and/or a vortex within the chamber so as to effect mixing of the fluid with the free flowing particles that are contained therein.

Figure 7:
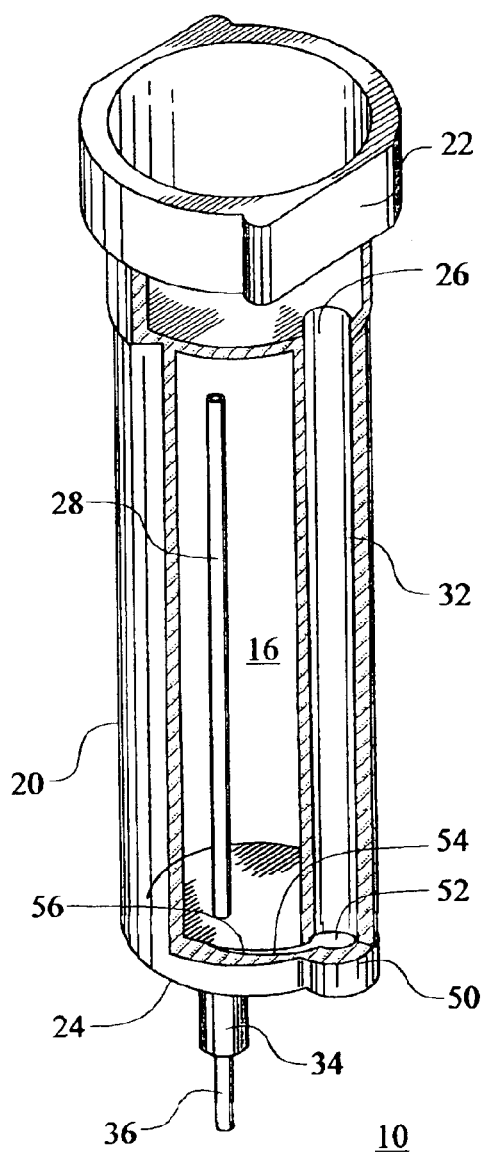
FIG. 7 is a perspective view, in partial section, of an alternative embodiment of the device of this invention in which a fluid delivery conduit is molded into the body of the device housing.
Figure 8:
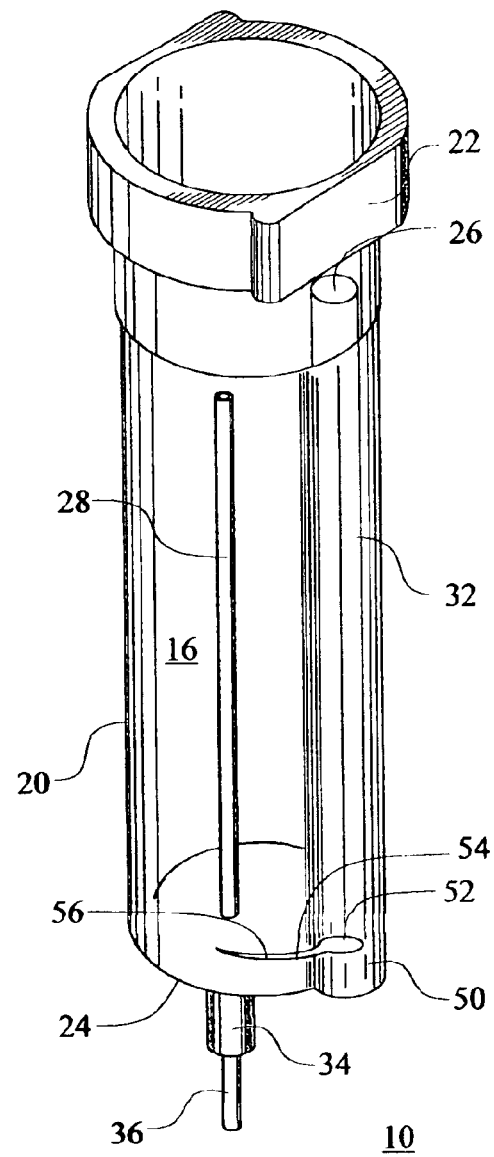
FIG. 8 is a perspective view of the device of FIG. 7 that has been molded from a transparent material.

FIG. 8 further illustrates additional detail of the construction of the device of FIG. 7 wherein the interior of the base of the device is revealed. More specifically, FIG. 8 depicts a device of the type illustrated in FIG. 7 fabricated from a plastic material. In this view, the detail of the base (24) is better revealed in that it further depicts the chute (50) and the ascending ramp (54) for channeling the fluid stream from the conduit into the chamber of the device. The chute can be modified as desired to optimize mixing and/or other operational objectives.

Molded Flow Control and Sealing Feature

FIG. 9 includes a feature of the invention wherein the feature provides a means for ensuring uni-directional flow of Gas Stream A and particulate matter (P of FIGS. 3 and 4) as well as providing a means for automatically sealing the apparatus 10 when the Gas Stream A ceases or the apparatus 10 is removed from the Airflow source (not shown). The feature, a molded, uni-directional flow and sealing apparatus 100, is of a design conducive to injection molding constraints and manufacturing economies. The molded, uni-directional flow and sealing apparatus 100 includes at least one slit 110 to allow Airflow (A of FIG. 4) to pass through as well as sealing the apparatus 10 to entrap the particulate matter P within the mixing chamber 16 while the apparatus is not in use. The function of the molded, uni-directional flow and sealing apparatus 100 is described in detail by FIGS. 10 and 10A.

FIGS. 10 and 10A illustrate the function of the molded, uni-directional flow and sealing apparatus 100. The molded, uni-directional flow and sealing apparatus 100 can be designed to be of a hemispherical shape, whereby the concave side 102 of the uni-directional flow and sealing apparatus 100 would be positioned towards the gas receiving port (26 of FIGS. 5, 6, 7, 8, and 9) of the apparatus 10 and the convex side 104 of the uni-directional flow and sealing apparatus 100 would be positioned towards the gas mixing chamber (16 of FIGS. 5, 6, 7, 8, and 9). The molded, uni-directional flow and sealing apparatus 100 comprising a flexible surface that is portioned into flexible sections 112 by the at least one slit 110. When Gas Stream A is applied to the molded, uni-directional flow and sealing apparatus 100, the Gas Stream A (differential in pressure across the surface) causes flexible sections 112 to elastically bend towards the gas mixing chamber (16 of FIGS. 5, 6, 7, 8, and 9) creating a passage 116 which allows Gas Stream A to pass through the molded, uni-directional flow and sealing apparatus 100 and into the gas mixing chamber 16. When Gas Stream A is removed from the molded, uni-directional flow and sealing apparatus 100, the lack of Gas Stream A (equilibrium in pressure across the surface) allows the flexible sections 112 to elastically return to the natural state of the molded, uni-directional flow and sealing apparatus 100, returning the flexible sections 112 towards the gas receiving port and closing the passage 116 (26 of FIGS. 5, 6, 7, 8, and 9); thus entrapping the particulate matter (P of FIGS. 3 and 4) within the gas mixing chamber 16. The molded, uni-directional flow and sealing apparatus 100 can be molded from a flexible material and stamped to provide the slits 110. The preferred embodiment would be a hemispherical design and include one (1) slit, forming an "I". The hemispherical design provides a geometrical means to limit the motion of the flexible sections 112 during the state lacking Gas Stream A to ensure the flexible sections 112 properly seal.

Method

In practicing the invention, the following method may be used. Reference is once again made to the illustrations of the preferred embodiments, specifically FIG. 4. A stream of gas A is delivered through gas-receiving port 26 and gas-delivery conduit 32 into chamber 16 from the gas air source (not shown). The gas stream A blows through the particulate matter P and causes the particulate matter P, to mix with the gas stream in chamber 16. The air and particle mixture M enter and pass through discharge conduit 28, discharge port 34 and directing tube 36, and exist the apparatus 10 to strike the target material T, this method is performed without generating heat, vibration, appreciable noise levels, and with a device free of any moving pans. In contrast to the prior art devices discussed herein which draw the particulate matter from a reservoir, under vacuum, into a hand piece (and are thus limited as to the amount of pressure that can be exerted an the air/particle stream), the direct blow-through of fluid into the particle mass allows for modulation of the pressure of the resultant stream over a much broader range and thus more precise delivery thereof to a delimited area of a target.

While the various embodiments of the invention have been described and illustrated herein, such is not intended, nor should it be construed a delimiting the scope of the invention, which is set forth in the following claims.

I claim as my invention:

1. A method of using a handheld apparatus for propelling particulate matter, the method comprising the steps:

placing particulate matter within a mixing chamber, said mixing chamber comprising a sidewall, a gas receiving port at a first end of the chamber and a discharge end wall at an opposite end of the chamber and sized to be used for abrading at least one tooth within a patient's mouth;

holding said mixing chamber in a manner by grasping the mixing chamber between two fingers of one hand during the application of said device for abrading at least one tooth within the patient's mouth, applying gas flow through a gas delivery conduit, whereby said gas delivery conduit would be disposed within the chamber and extend into the mixing chamber further applying gas into said mixing chamber; and discharging a mixture of gas flow and said particulate matter through a discharge port in said discharge end wall for abrading at least one tooth within a patient's mouth.

2. The method of claim 1, wherein the size and shape of the handheld apparatus for propelling particulate matter resembles that of a syringe, wherein a shape of a syringe comprises a cylindrical body, a discharge end wall comprising a discharge port and positioned at one end of the cylindrical body, wherein said discharge end wall can be flat, tapered or curved, and a coupling mechanism positioned opposing said discharge end wall.

3. The method of claim 1, the method further comprising the step of discharging the mixture or gas flow and said particle matter through an elongated particle directing tube, said elongated particle directing tube being positioned at least partially external to said mixing chamber and in fluid communication with said discharge conduit.

4. The method of claim 3, wherein said elongated particle directing tube is contiguous with said discharge conduit.

5. The method of claim 3, the method further comprising the step of manually placing a bend in said elongated particle directing tube.

6. The method of claim 1, the method further comprising the step of identifying the particulate matter by a color-coding.

7. The method of claim 1, the method further comprising the step of maintaining particulate matter within said mixing chamber by coupling at least one of a gas delivery port cap and a discharge end cap to said handheld apparatus for propelling particulate matter.

8. The method of claim 7, the method further comprising the step of identifying the particulate matter by a color-coding.

9. The method of claim 2, the method further comprising the step of coupling an air supply to an attachment area located proximate said gas receiving port to the apparatus.

10. The method of claim 1, the method further comprising the step of passing the gas flow through said gas delivery conduit, into said mixing chamber, then discharging said mixture of gas flow and particulate matter through a discharge conduit, wherein said discharge conduit is in fluid communication with a discharge port in said discharge end wall.

11. The method of claim 10, the method further comprising the step of passing the gas flow through said gas delivery conduit, into said mixing chamber, then into said discharge conduit, whereby an exit orifice of said gas delivery conduit is positioned beyond an entrance orifice of said discharge conduit respective to the direction of said gas flow.

12. The method of claim 10, the method further comprising the step of discharging said gas flow from said gas delivery conduit within said mixing chamber, wherein an exit orifice of said delivery conduit is positioned off-center of said mixing chamber.

13. The method of claim 10, the method further comprising the step of passing said gas flow into said discharge conduit within said mixing chamber, wherein an entrance orifice of said discharge conduit is positioned off-center of said mixing chamber.

14. A method for propelling particulate matter using a handheld apparatus, the method comprising the steps:

propelling particulate matter from a mixing chamber, wherein said mixing chamber is sterile and pre-filled with particulate matter and designed to be non-conducive to being refilled holding said mixing chamber in a manner by grasping the mixing chamber between two fingers of one hand during the application of said device for abrading at least one tooth within the patient's mouth, passing a gas flow through a gas delivery conduit, whereby said gas delivery conduit is disposed within said mixing chamber and extends in fluid communication into said mixing chamber and towards the gas receiving port;

passing said gas flow into said mixing chamber to create a gas and particulate matter mix, passing said gas flow and particulate matter mix through at least one of a discharge port in the discharge end wall, an elongated particle-directing tube disposed external to the mixing chamber, an elongated particle-directing tube disposed through the discharge port in the discharge end well;

temporarily containing said particulate matter within said mixing chamber by coupling at least one of a sealing mechanism to said discharge port and a sealing mechanism to said gas delivery conduit; and disposing of said mixing chamber at least one of completion of use and upon exhaustion of particulate matter.

15. The method or claim 14, the method further comprising the step or discharging said gas flow from said gas delivery conduit within said mixing chamber, wherein an exit orifice of said delivery conduit is positioned off-center of said mixing chamber.

16. The method of claim 14, wherein the size and shape of the handheld apparatus for propelling particulate matter resembles that of a syringe, wherein a shape of a syringe comprises a cylindrical body, an end wall at one end of the cylindrical body (discharge end wall and discharge port) that can be flat, tapered or curved, and a coupling mechanism (opposing end of the end wall).

17. The method or claim 14, the method further comprising the step of discharging the mixture or gas flow and said particle matter through an elongated particle directing tube, said elongated particle directing tube being positioned at least partially external to said mixing chamber and in fluid communication with said discharge conduit.

18. The method of claim 17, wherein said elongated particle directing tube is contiguous with said discharge conduit.

19. The method of claim 14, the method further comprising the step of placing a bend in said elongated particle directing tube.

20. The method of claim 14, the method further comprising the step of identifying the particulate matter by a color-coding.

21. The method of claim 14, the method further comprising the step of maintaining particulate matter within said mixing chamber by coupling at least one of a gas delivery port cap and a discharge end cap to said handheld apparatus for propelling particulate matter.

22. The method of claim 21, the method further comprising the step of identifying the particulate matter by a color-coding.

23. The method of claim 16, the method further comprising the step of coupling an air supply to an attachment area located proximate said gas receiving port to the apparatus.

* * * * *